(12) United States Patent  
Shimazu

(10) Patent No.: US 11,911,020 B2  
(45) Date of Patent: Feb. 27, 2024

(54) NEEDLE HOLDER FOR ENDOSCOPE, SUTURE SET, AND SUTURE SYSTEM

(71) Applicant: OLYMPUS CORPORATION, Hachioji (JP)

(72) Inventor: Akihiro Shimazu, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 322 days.

(21) Appl. No.: 17/238,544

(22) Filed: Apr. 23, 2021

(65) Prior Publication Data

US 2021/0236116 A1   Aug. 5, 2021

Related U.S. Application Data

(63) Continuation of application No. 16/053,314, filed on Aug. 2, 2018, now Pat. No. 11,020,105, which is a (Continued)

(51) Int. Cl.
*A61B 1/018* (2006.01)
*A61B 17/04* (2006.01)
(Continued)

(52) U.S. Cl.
CPC .......... *A61B 17/0469* (2013.01); *A61B 1/018* (2013.01); *A61B 17/062* (2013.01); *A61B 2017/0034* (2013.01)

(58) Field of Classification Search
CPC ... A61B 17/0469; A61B 17/062; A61B 1/018; A61B 2017/0034
See application file for complete search history.

(56) References Cited

U.S. PATENT DOCUMENTS 5,257,999 A   11/1993  Slanetz, Jr.
5,919,202 A * 7/1999  Yoon .................. A61F 6/20
                                                606/205
(Continued)

FOREIGN PATENT DOCUMENTS

CN   2562734 Y   7/2003
EP   2221006 A1  8/2010
(Continued)

OTHER PUBLICATIONS

May 24, 2016 International Search Report issued in International Patent Application No. PCT/JP2016/055678.
(Continued)

*Primary Examiner* — Timothy J Neal
*Assistant Examiner* — William B Chou
(74) *Attorney, Agent, or Firm* — Oliff PLC

(57) ABSTRACT

A needle holder includes: a flexible sheath portion which is capable of being inserted into an instrument channel of a flexible endoscope; a first grasping member which is rotatably coupled with a distal end portion of the flexible sheath portion; and a second grasping member which is provided in the distal end portion of the flexible sheath portion. In a state where a curved needle is grasped by a first grasping surface of the first grasping member and a second grasping surface of the second grasping member, the second grasping surface inclines such that a grasped region of the curved needle that is grasped by the first grasping surface and the second grasping surface is positioned between a distal end of the second grasping member and a needle tip of the curved needle in a direction of a center axis of the second grasping member.

19 Claims, 12 Drawing Sheets

Related U.S. Application Data continuation of application No. PCT/JP2016/055678, filed on Feb. 25, 2016.

(51) Int. Cl.
 *A61B 17/062* (2006.01)
 *A61B 17/00* (2006.01)

(56) References Cited

U.S. PATENT DOCUMENTS

| | | | |
|---|---|---|---|
| 5,951,587 A | | 9/1999 | Qureshi et al. |
| 6,143,005 A | * | 11/2000 | Yoon ................ A61B 17/12013 606/148 |
| 6,171,316 B1 | | 1/2001 | Kovac et al. |
| 9,504,464 B2 | | 11/2016 | Gellman et al. |
| 2003/0181924 A1 | | 9/2003 | Yamamoto et al. |
| 2008/0188868 A1 | | 8/2008 | Weitzner et al. |
| 2010/0217286 A1 | | 8/2010 | Gerber et al. |
| 2012/0123471 A1 | | 5/2012 | Woodard, Jr. et al. |
| 2012/0271329 A1 | | 10/2012 | Nakamura |
| 2012/0283754 A1 | | 11/2012 | Murillo et al. |
| 2012/0289975 A1 | | 11/2012 | Martin et al. |
| 2013/0245643 A1 | | 9/2013 | Woodard, Jr. et al. |
| 2013/0282027 A1 | | 10/2013 | Woodard, Jr. et al. |
| 2017/0119371 A1 | | 5/2017 | Mims et al. |

FOREIGN PATENT DOCUMENTS

| | | |
|---|---|---|
| JP | H01-129843 A | 5/1989 |
| JP | H11-276492 A | 10/1999 |
| JP | 2005-278681 A | 10/2005 |
| JP | 2009-183690 A | 8/2009 |
| JP | 2012-228311 A | 11/2012 |
| JP | 2013-529981 A | 7/2013 |
| JP | 2014-500756 A | 1/2014 |
| WO | 2011/163634 A1 | 12/2011 |
| WO | 2012/068004 A1 | 5/2012 |

OTHER PUBLICATIONS

Jun. 20, 2017 Office Action issued in Japanese Patent Application No. 2017-526002.
Jul. 15, 2019 Search Report issued in European Patent Application No. 16891492.7.
Jun. 2, 2020 Chinese Office Action issuedd in Chinese Patent Application No. 201680081307.6.
Oct. 9, 2020 Office Action Issued in U.S. Appl. No. 16/053,314.
Feb. 10, 2021 Office Action issued in Chinese Patent Application No. 201680081307.6.
Feb. 1, 2021 Notice of Allowance issued in U.S. Appl. No. 16/053,314.

* cited by examiner

NEEDLE HOLDER FOR ENDOSCOPE, SUTURE SET, AND SUTURE SYSTEM

This is a Continuation of application Ser. No. 16/053,314 filed Aug. 2, 2018, which in turn is a Continuation application based on PCT/JP2016/055678, filed on Feb. 25, 2016. The disclosure of the prior applications is incorporated herein by reference.

TECHNICAL FIELD

The present invention relates to a needle holder for endoscope, a suture set, and a suture system.

BACKGROUND ART

Conventionally, a needle holder that is used for suturing a tissue in a body is known (for example, Japanese Unexamined Patent Application, First Publication No. 2012-228311). A suture instrument for suturing the tissue of the body under a laparoscope in an operation using the laparoscope is known (for example, Japanese Translation of PCT International Application Publication No. 2014-500756 and Japanese Translation of PCT International Application Publication No. 2013-529981).

The needle holder having an insertion portion that is flexible and is capable of being inserted into an instrument channel of a flexible endoscope is known (for example, Japanese Unexamined Patent Application, First Publication No. 2009-183690).

SUMMARY OF INVENTION

A first aspect of the present invention is a needle holder that include: a flexible sheath portion which is longitudinal, flexible, and capable of being inserted into an instrument channel of a flexible endoscope; a first grasping member which includes a first grasping surface and is rotatably coupled with a distal end portion of the flexible sheath portion; and a second grasping member which includes a second grasping surface and is provided in the distal end portion of the flexible sheath portion. The second grasping surface inclines from a proximal end of the second grasping surface toward a distal end side of the second grasping surface, the distal end of the second grasping surface is closer to the first grasping member than the proximal end of the second grasping surface, and in a state where a grasped region of a curved needle is grasped by the first grasping surface and the second grasping surface, a needle tip of the curved needle positions closer to a proximal end of the flexible sheath portion than the grasped region of the curved needle.

The second grasping surface may incline in a range of 5° or more and 20° or less from the center axis of the flexible sheath portion.

The second grasping member may include a projection portion that projects from a distal end of the second grasping surface to the first grasping member side.

The second grasping member may include a groove part that extends from a distal end of the second grasping surface toward a proximal end of the second grasping surface. The width of the groove part may be larger than the width of the first grasping surface in a direction perpendicular to a center axis of the flexible sheath portion.

A second aspect of the present invention is a suture set that includes the needle holder of the above aspect; and a curved needle that is grasped by the needle holder. The curved needle includes a flat portion which is at least a portion of an outer circumference of the curved needle and is formed flatly in a cross-section perpendicular to a center axis extending along an arc of the curved needle, and in a state where the grasped region of the curved needle is grasped by the first grasping surface of the first grasping member and the second grasping surface of the second grasping member, an orientation of the curved needle is restricted such that the needle tip is positioned closer to a proximal end side than the flat portion by contacting the flat portion to at least one of the first grasping surface and the second grasping surface.

A third aspect of the present invention is a suture system which includes: the needle holder; and an endoscope that includes: an instrument channel into which the flexible sheath portion is inserted, and an imager that is configured to capture at least the first grasping member and the second grasping member among the needle holder projected from a distal end of the instrument channel. In a state where the curved needle is grasped between the first grasping member and the second grasping member, the second grasping surface inclines with an angle in which an orientation of the curved needle is configured to restrict such that a first straight-line distance from the imager to a center portion of the curved needle is equivalent to a second straight-line distance from the imager to a needle tip of the curved needle.

DESCRIPTION OF EMBODIMENTS

First Embodiment

Figure 1:
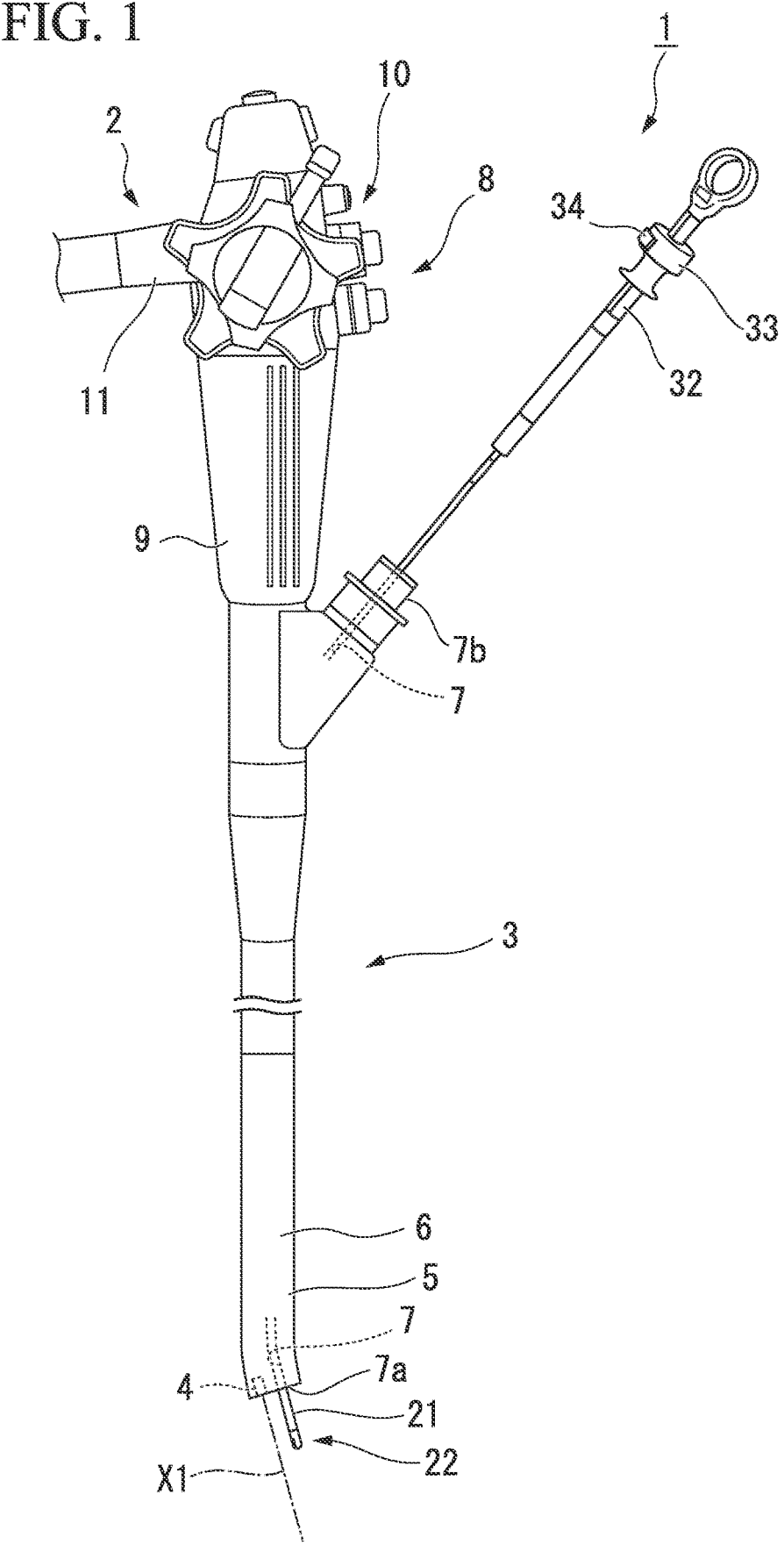
FIG. 1 is an overall view showing a suture system of a first embodiment of the present invention.
Figure 2:
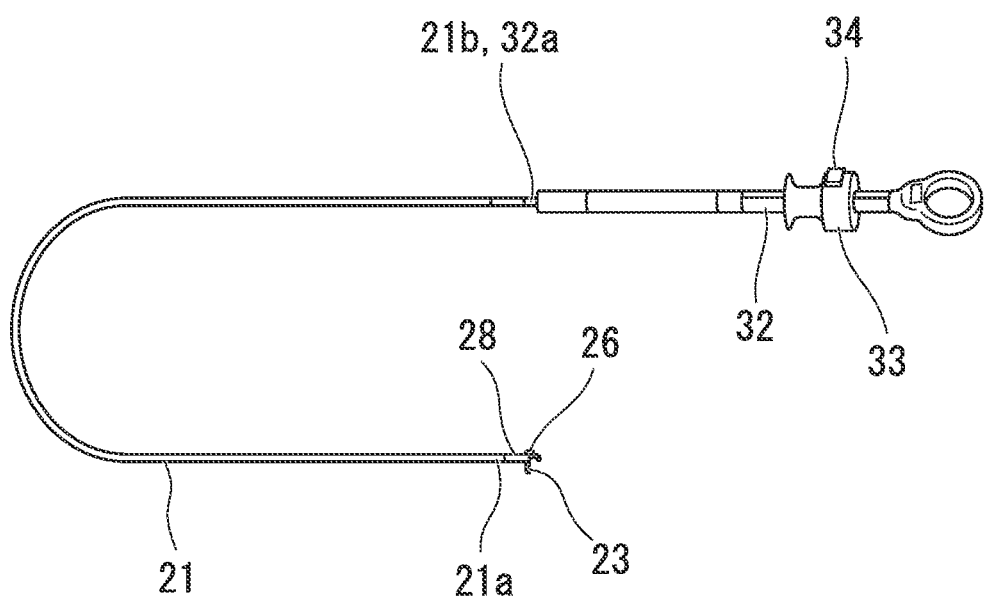
FIG. 2 is an overall view showing a needle holder in the suture system.
Figure 3:
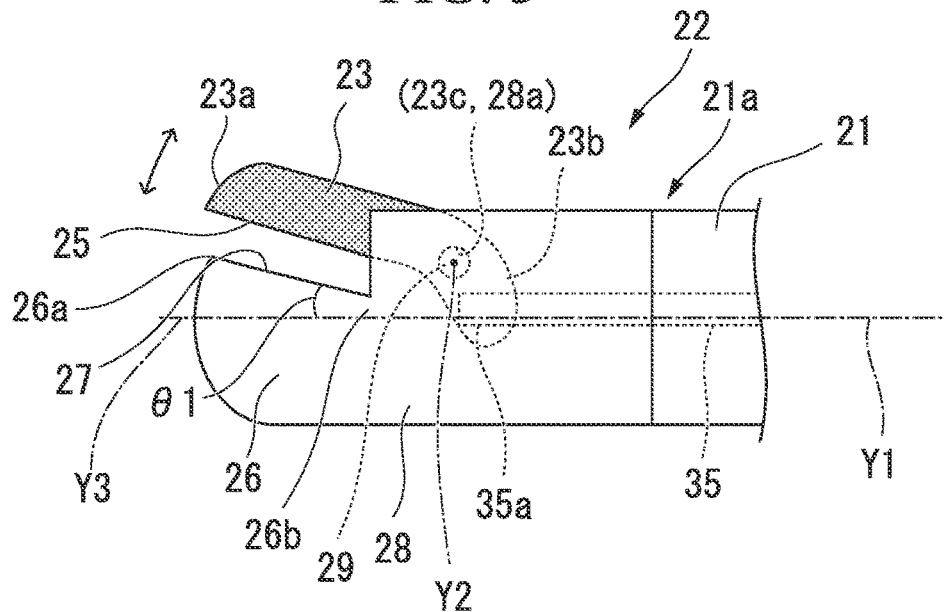
FIG. 3 is a lateral view showing a treatment portion of the needle holder.
Figure 4:
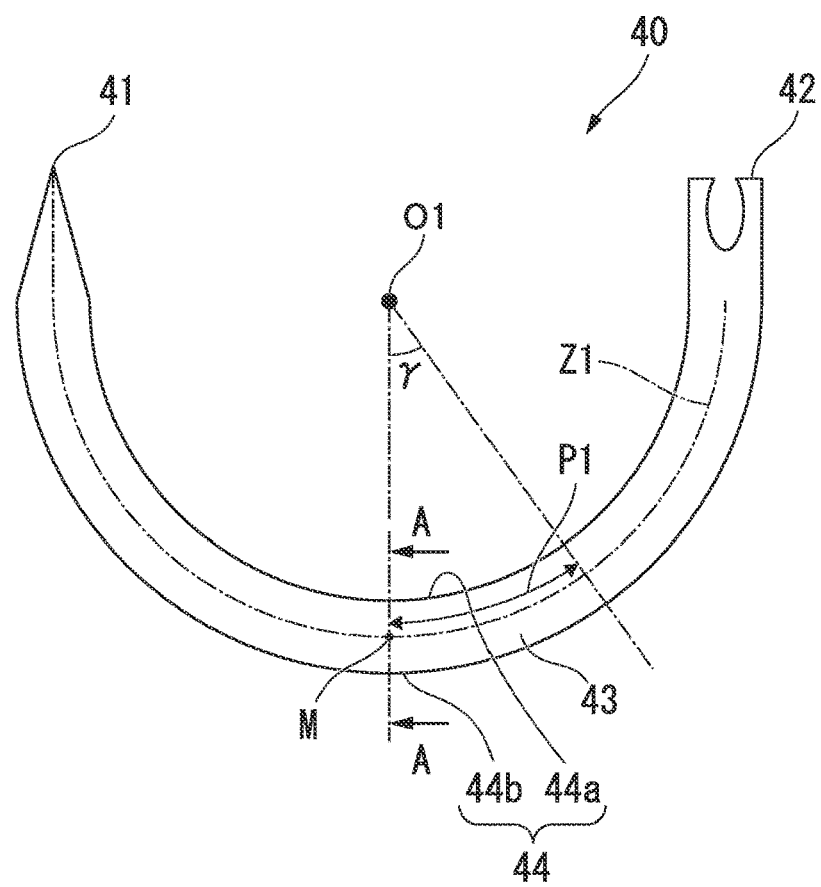
FIG. 4 is a lateral view of a grasped curved needle by the needle holder.
Figure 5:
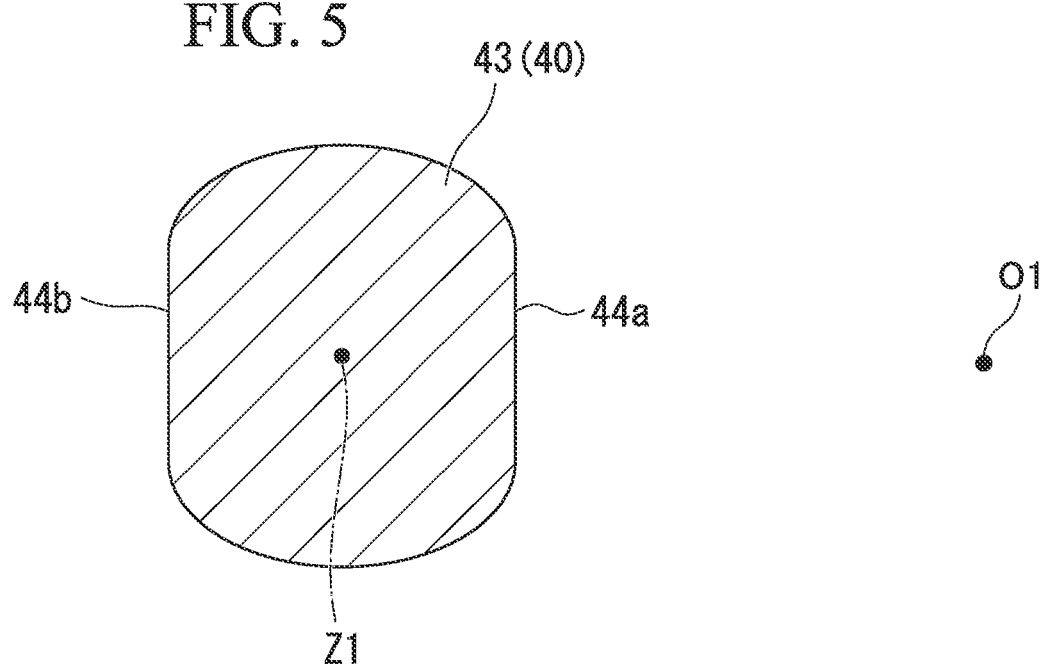
FIG. 5 is a cross-sectional view in A-A line of FIG. 4.
Figure 6:
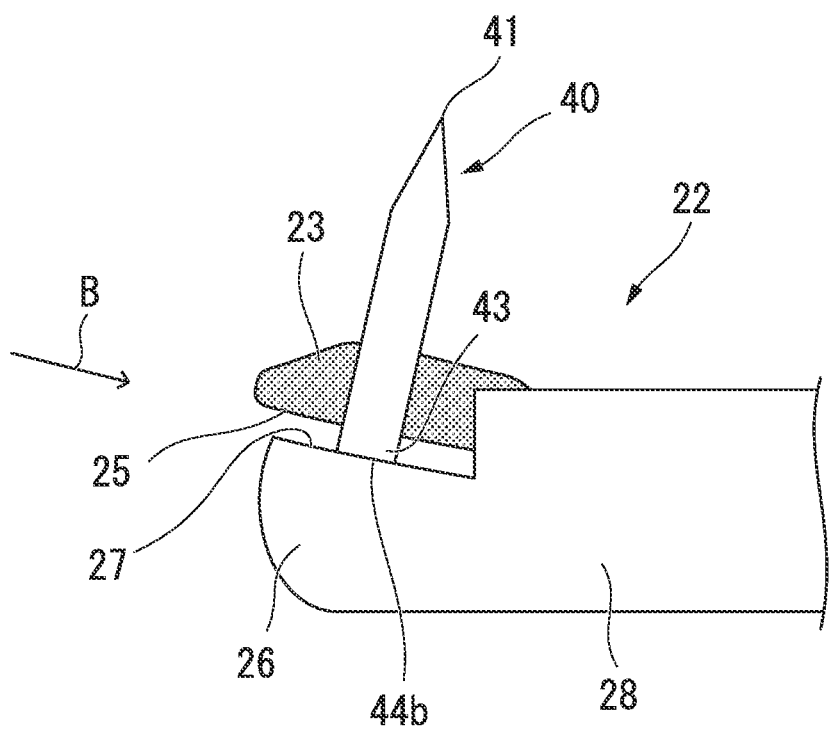
FIG. 6 is a view showing a state where the curved needle is stably grasped by the needle holder.
Figure 7:
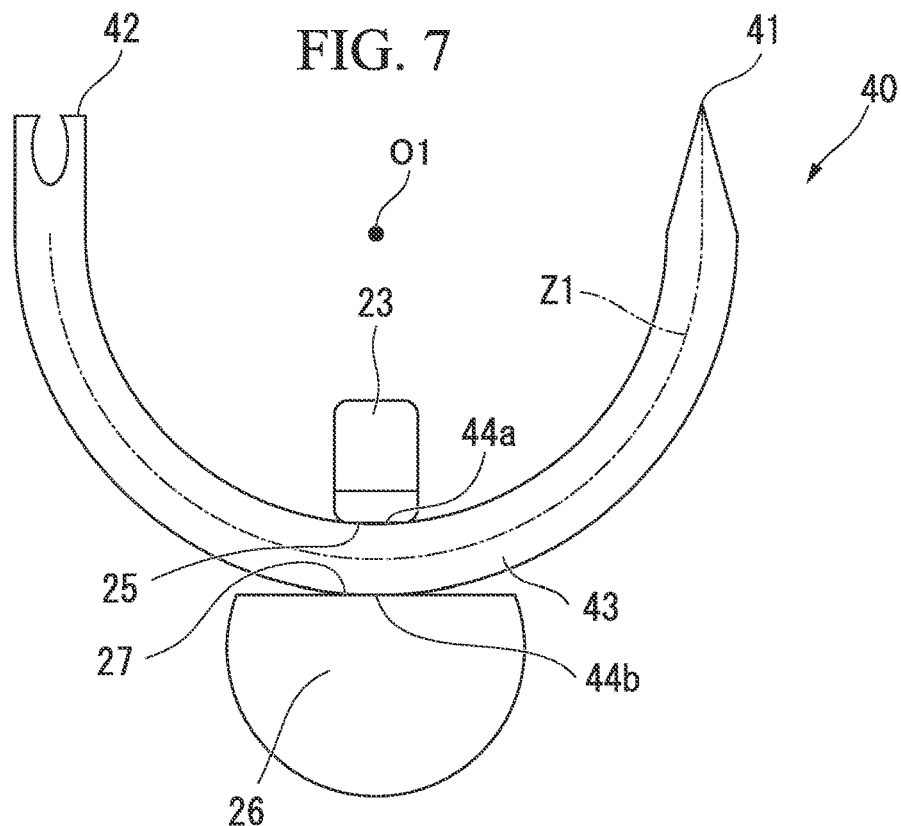
FIG. 7 is a view showing a state where the curved needle is stably grasped by the needle holder from a B direction of the FIG. 6.

One embodiment of the present invention will be described. FIG. 1 is an overall view showing a suture system 1 of a present embodiment. FIG. 2 is an overall view showing a needle holder 20 in the suture system 1. FIG. 3 is a lateral view showing a treatment portion 22 of the needle holder 20. FIG. 4 is a lateral view of a grasped curved needle 40 by the needle holder 20. FIG. 5 is a cross-sectional view in A-A line of FIG. 4. FIG. 6 is a view showing a state where the curved needle 40 is stably grasped by the needle holder 20. FIG. 7 is a view showing a state where the curved needle 40 is stably grasped by the needle holder 20 from a B direction of the FIG. 6.

As shown in FIGS. 1 to 4, the suture system 1 of the present embodiment includes a flexible endoscope 2, suture holder 20, and a curved needle 40.

The flexible endoscope 2 includes an insertion portion 3, and a manipulation portion 8.

The insertion portion 3 includes an imager 4, an active bent portion 5, and a flexible portion 6 from a distal end in this order. An instrument channel 7 for inserting the needle holder 20 of the present embodiment is provided inside of the insertion portion 3. A distal end opening 7a of the instrument channel 7 is provided in the distal end of the insertion portion 3.

The imager 4 is capable of imaging a part that is a treatment target. The imager 4 is arranged in the distal end part of the insertion portion 3 such that an optical axis X1 extends in a longitudinal direction of the insertion portion 3. The imager 4 can image a first grasping member 23 and a second grasping member 26 (described later) of the needle holder 20 in a state where the needle holder 20 that is inserted into the instrument channel 7 is projected from the distal end opening 7a of the instrument channel 7.

The active bent portion 5 is capable of actively bending in accordance with the manipulation which the operator of the flexible endoscope 2 performs for the manipulation portion 8.

The manipulation portion 8 is connected to the flexible portion 6. The manipulation portion 8 includes a grip 9 that is grasped by the operator, an input portion 10 that receives the manipulation for moving the active bent portion 5, a proximal end opening portion 7b of the instrument channel 7, and a universal cord 11 for outputting the image that the imager 4 captures outside. The universal cord 11 that is provided in the manipulation portion 8 is capable of connecting to a display apparatus (not shown) via an image processing device (not shown).

A configuration of the flexible endoscope 2 of the present embodiment is not limited by the above configuration. For example, a known flexible endoscope that includes one or more channel may be appropriately selected as a flexible endoscope that is capable of using with the needle holder 20. When the channel can be attached to the flexible endoscope as an external channel, the flexible endoscope can be attached to an external channel instead of the channel into which the needle holder 20 of the present embodiment is inserted, the channel may be not formed in the flexible endoscope.

A shown in FIG. 2, the needle holder 20 includes a flexible tube 21 that is flexible and longitudinal, a therapeutic portion 22 that is arranged in a distal end 21a of the flexible tube 21, an operating portion 31 that is arranged in a proximal end 21b of the flexible tube 21, and an operating wire 35 that is arranged inside of the flexible tube 21 and that is connected to the operating portion 31 and the therapeutic portion 22.

The flexible tube 21 is capable of being inserted into the instrument channel 7 of the flexible endoscope 2 shown in FIG. 1. A distal end 21a of the flexible tube 21 is capable of advancing from the distal end opening 7a of the instrument channel 7 and retracting into the instrument channel 7 in a state where the flexible tube 21 is inserted into the instrument channel 7. The distal end 21a of the flexible tube 21 is capable of advancing into an imaging field of view of the imager 4 of the flexible endoscope 2 and is captured by the imager 4.

As shown in FIGS. 2, 3, and 6, the therapeutic portion 22 includes the first grasping member 23 and the second grasping member 26 for grasping the curved needle 40, and a connecting part 28 and a coupling shaft 29 that are coupled with the first grasping member 23 and the second grasping member 26 such that the first grasping member 23 is capable of opening and closing with respect to the second grasping member 26.

The first grasping member 23 is coupled with the distal end 21a of the flexible tube 21 via the connecting part 28 and the coupling shaft 29. A proximal end 23b of the first grasping member 23 is connected to a distal end 35a of the operating wire 35. The first grasping member 23 includes a hole portion 23c for coupling the first grasping member 23 with the connecting part 28 via the coupling shaft 29 between the distal end 23a and the proximal end 23b of the first grasping member 23. A surface that is faced on the second grasping member 26 in the first grasping member 23 includes a first grasping surface 25 that is capable of contacting with the curved needle 40. The first grasping surface 25 is parallel to a second grasping surface 27 (described later) of the second grasping member 26 in a state where the curved member 40 is grasped by the first grasping member 23 and the second grasping member 26.

The second grasping member 26 is coupled to the distal end 21a of the flexible tube 21 via the connecting part 28 so as to extend in a center line (center axis) Y1 direction of the flexible sheath portion 21. In the present invention, the second grasping member 26 and the connecting part 28 are integrally molded. The second grasping member 26 includes the second grasping surface 27 that inclines with respect to the center line Y1 of the flexible tube 21 and is faced on a proximal end 26b side of the second grasping member 26. That is, as shown in FIGS. 3 and 6, in a side view of a direction in which the coupling shaft 29 extends, the second grasping surface 27 (line connecting a proximal end of the second grasping surface 27 with a distal end) inclines so as to be a sharp angle at a proximal end side of the second grasping surface 27 with respect to a line parallel to a line Y3 that is an extended line of the center line Y1 of the flexible tube 21. In the state where the curved needle 40 grasped by the first grasping surface 25 and the second grasping surface 27, a grasped region (center region P1 including a grasping portion P2 to be later) of the curved needle 40 grasped by the first grasping surface 25 and the second grasping surface 27 is positioned between the distal end 26*a* of the second grasping member 26 and a needle tip 41 of the curved needle 40 in the center axis direction of the flexible tube 21.

Specifically, the second grasping surface 27 inclines from a proximal end 27*b* of the second grasping surface 27 toward a distal end 27*a* side such that a distal end 27*a* side of the second grasping surface 27 approach the first grasping member 23 with respect to the center line Y1 of the flexible tube 21. For example, the second grasping surface 27 may incline linearly when viewing from the longitudinal axis direction of a rotation axis Y2.

The second grasping surface 27 inclines in a predetermined angle θ1 that is a range of 5° (degree) or more and 20° (degree) or less with respect the line Y3 that is an extended line of the center line Y1 of the flexible tube 21 when viewing from a direction in which the rotation axis Y2 of the therapeutic portion 22 extends. The second grasping surface 27 is different from a convexoconcave for a slip resistance, and is provided at a predetermined region in the vicinity of the distal end 26*a* of the second grasping member 26 as a flat surface for grasping the curved needle 40.

The connecting part 28 includes a hole portion 28*a* for coupling and fixing the coupling shaft 29. The center line Y2 of the coupling shaft 29 coupled with the connecting part 28 extends in a direction perpendicular to the line Y3 that is an extended line of the center line Y1 of the flexible tube 21. The first grasping member 23 is capable of rotating around the rotation axis Y2 that is a line as the rotation axis Y2 (the rotation axis Y2 of the coupling shaft 29) extending in a direction that is perpendicular to the center line Y1 of the flexible tube 21 because the first grasping member 23 and the second grasping member 26 are coupled by the hole portions 23*c*, 28*a* and the coupling shaft 29. Thereby, the first grasping member 23 is capable of opening and closing with respect to the second grasping member 26. That is, the therapeutic portion 22 of the present embodiment is a single swing therapeutic portion in which the first grasping member 23 is open and close with respect to the second grasping member 26 coupled with the distal end 21*a* of the flexible tube 21 via the connecting part 28 and the coupling shaft 29.

As shown in FIG. 2, the operating portion 31 includes an operating portion main body 32, a slider 33, a fixing mechanism (ratchet mechanism or the like, not shown) which limits that a slider 33 moves to the distal end side with respect to the operating portion main body 32, and a release button 34 of the fixing mechanism.

A distal end 32*a* of the operating portion main body 32 is fixed to the proximal end 21*b* of the flexible tube 21. The slider 33 is coupled so as to be advanced and retracted in a longitudinal direction of the operating portion main body with respect to the operating portion main body 32. Furthermore, the slider 33 is coupled with a proximal end 35*b* of the operating wire 35. The operating wire 35 can be moved along the center line Y1 of the flexible tube 21 by advancing and retracting the slider 33 along the operating portion main body 32. In the present invention, the operating wire 35 can be towed toward the operating portion 31 side by moving the slider 33 toward the proximal end side along the operating portion main body 32. The slider 33 is capable of limiting the movement toward the proximal end side at the predetermined position by the fixing mechanism. Accordingly, the slider 33 is locked in a state where the slider 33 tows the operating wire 35, and the state where the operating wire 35 tows can be maintained.

As shown in FIGS. 2 and 3, the operating wire 35 is a flexible wire for transmitting operating force amount for performing the opening-closing operation of the first grasping member 23 with respect to the second grasping member 26 form the operating portion 31 to the first grasping member 23. The distal end 35*a* of the operating wire 35 is connected to the proximal end 23*b* of the first grasping member 23. The proximal end 35*b* of the operating wire 35 is connected to the slider 33 of the operating portion 31. It is difficult for the operating wire 35 to elongate in the longitudinal direction of the operating wire 35, and the operating wire 35 can deform such that the longitudinal axis line of the operating wire 35 bends. The operating wire 35 is towed toward the operating portion 31 side, thereby the first grasping member 23 moves to a closing direction with respect to the second grasping member 26. The operating wire 35 is towed toward the operating portion 31 side, thereby the grasping force amount of the curved needle 40 by the first grasping member 23 and the second grasping member 26 occurs.

As shown in FIG. 4 to FIG. 7, the curved needle 40 is an arc shape having a predetermined curvature. The curved needle 40 includes the needle tip 41 that is capable of being inserted into the tissue, a needle root part 42 that is coupled with the suture thread, and a needle main body 43 that is arranged between the needle tip 41 and the needle root part 42 so as to connect the needle tip 41 and the needle root part 42.

As shown in FIG. 4 and FIG. 5, the needle main body 43 (curved needle 40) includes a flat portion 44 in which at least a portion of an outer circumference of the curved needle 40 is formed flatly in a cross-section perpendicular to the center line Z1 extending along an arc of the curved needle 40.

Thereby, in a state where the curved needle 40 is grasped by the first grasping surface 25 and the second grasping surface 27, the flat portion 44 is contacted to at least one of the first grasping surface 25 and the second grasping surface 27, thereby an orientation of the curved needle 40 can be restricted such that the needle tip 41 is positioned closer to the proximal end side than the flat portion 44.

The flat portion 44, more specifically, includes a first flat portion 44*a* and a second flat portion 44*b*.

The first flat portion 44*a* is formed inside (closer to a center of curvature O1 of the curved needle 40) of a bending part of the curved needle 40 among the outer circumference of the needle main body 43 in a cross-section perpendicular to the center line Z1 extending along the arc of the curved needle 40.

The second flat portion 44*b* is formed outside (away from the center of curvature O1 of the curved needle 40) of a bending part of the curved needle 40 among the outer circumference of the needle main body 43 in a cross-section perpendicular to the center line Z1 extending along the arc of the curved needle 40.

Figure 8:
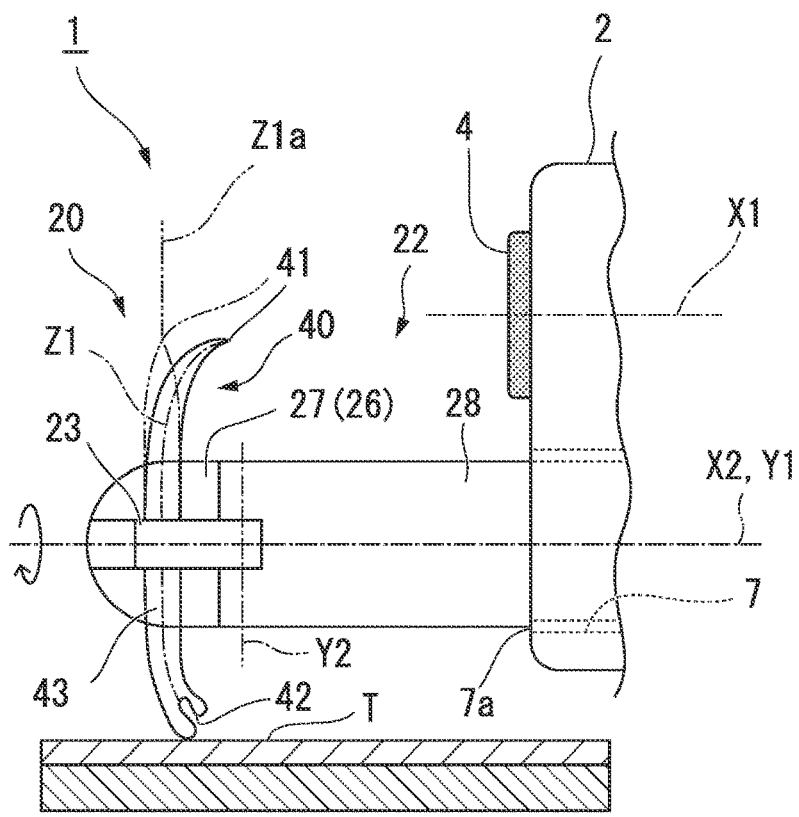
FIG. 8 is a view showing a state where the needle holder is inserted into a flexible endoscope.

The operation of the suture system 1 of the present embodiment will be described. FIG. 8 is a view showing a state where the needle holder 20 is inserted into a flexible endoscope 2.

In a state where the tissue in the body is sutured using the suture system 1 of the present embodiment. The curved needle 40 introduced to a vicinity of a target to be sutured is grasped using the needle holder 20 under the endoscope.

To grasp the curved needle 40 at the orientation appropriate for suturing, an operator of the needle holder 20 grasps the curved needle 40 using the operating portion 31 such that the needle main body 43 of the curved needle 40 is position between the first grasping member 23 and the second grasping member 26. For example, the operator slightly tows the slider 33 toward the proximal end side of the operating portion 31 and moves the first grasping member 23 toward the second grasping member 26 side, thereby the needle main body 43 of the curved needle 40 is grasped. As shown in FIG. 6 and FIG. 7, in a state where the first flat portion 44a is contacted to the first grasping surface 25 and the second flat portion 44b is contacted to the second grasping surface 27, a position of the carved needle 40 becomes stable in a state where the needle tip 41 is inclined toward the proximal end slightly. In this state, when the operator further tows the slider 33, the movement of the distal end side of the slider 33 is limited by the fixing mechanism. Accordingly, the state where the curved needle 40 is grasped by the first grasping member 23 and the second grasping member 26 is held such that the curved needle 40 does not rotate.

In the present invention, the curved needle 40 can be grasped by the first grasping member 23 and the second grasping member 26 such that the second flat portion 44b is contacted to the first grasping surface 25 and the first flat portion 44a is contacted to the second grasping surface 27. However, a preferable grasping state of the curved needle 40 of the present embodiment is the state where the first flat portion 44a is contacted to the first grasping surface 25 and the second flat portion 44b is contacted to the second grasping surface 27.

In a state where the curved needle 40 is grasped by the needle holder 20 such that the first flat portion 44a is contacted to the first grasping member 23 and the second flat portion 44b is contacted to the second grasping member 26, when the movement of the slider 33 is limited such that the slider 33 does not move to the distal end side, the second grasping member 26 restricts the orientation of the curved needle 40 such that the needle tip 41 is positioned closer to the proximal end than the second flat portion 44b.

In the present embodiment, a center line X2 of the distal end opening 7a of the instrument channel 7 of the flexible endoscope 2 is away from the optical axis X1 so as to be approximately parallel to the optical axis X1 of the imager 4. Thereby, the distal end portion of the needle holder 20 that is projected from the distal end opening 7a of the instrument channel 7 is projected to the distal end side approximately parallel to the optical axis X1. In this state, as shown in FIG. 8 by a chain double-dashed line, when the curved needle 40 is grasped by the needle holder 20 such that a center line Z1a of the curved needle 40 is positioned in a plane perpendicular to the line Y3 that is an extended line of the center line Y1 of the flexible tube 21, there is a case in which it may seem that a distance to the needle main body 43 of the curved needle 40 and a distance to the needle tip 41 of the curved needle 40 are extremely different in the image captured by the imager 4 of the flexible endoscope 2.

In a case in which the needle holder 20 is inserted into the flexible endoscope 2 and the tissue is sutured by the needle holder 20, in a puncture process to the tissue to be sutured, the needle tip 41 of the curved needle 40 moves from a position closer to the optical axis X1 (see FIG. 8) toward the tissue T away from the optical axis X1 because the target tissue is treated during captured the target tissue to be sutured in a lower side of the endoscope image. In this time, as shown in FIG. 8 by a chain double-dashed line, when the center line Z1a of the curved needle 40 is positioned in a plane perpendicular to the line Y3 that is an extended line of the center line Y1, it seems that the needle tip 41 moves further away from an actual positon on the endoscope image. Consequently, when the tissue is sutured under the endoscope in the state where the curved needle 40 is grasped by the needle holder 20 such that the center line Z1 of the curved needle 40 is positioned in a plane perpendicular to the line Y3, there is a possibility that the operator of the needle holder 20 deeply inserts the needle tip 41 into the tissue than intended by misidentifying the position of the needle tip 41 in the optical axis X1 direction of the imager 4.

When the tissue is sutured under the endoscope in the state where the curved needle 40 is grasped by the needle holder 20 such that a center line Z1a of the curved needle 40 is positioned in a plane perpendicular to the line Y3 that is an extended line of the center line Y1 of the flexible tube 21, an angle in which the needle tip 41 inserts into the tissue is deep than the intended angle and there is a possibility that the tissue is inserted more deeply than necessary because the puncture resistance of the needle tip 41 is more reduced than intended.

On the other hand, in the present invention, as shown in FIG. 6, it seems that a distance to the needle tip 41 is nearly the same as the distance to the needle main body 43 on the image captured by the imager 4 of the flexible endoscope 2 because the needle tip 41 faces the proximal end side more than the second flat portion 44b. Consequently, the distance between the needle tip 41 of the curved needle 40 grasped by the needle holder 20 of the present embodiment and the imager 4 can be easily obtained. As a result, according to the suture system 1 of the present embodiment, the possibility of inserting the curved needle 40 into the tissue more deeply than intended can be reduced.

In the present embodiment, the suture system 1 has the curved needle 40 that includes the first flat portion 44a and the second flat portion 44b, thereby in addition to contacting the second flat portion 44b to the second grasping surface 27 and restricting the orientation of the curved needle 40, the orientation of the curved needle 40 is capable of restricting by contacting the first flat portion 44a to the first grasping surface 25. Consequently, according to the suture system 1 of the present embodiment, compared to a case where only the second flat portion 44b is formed in the curved needle 40, the curved needle 40 can be held with more stability. The suture set has the needle holder 20 of the present invention and the curved needle 40 including the first flat portion 44a and the second flat portion 44b performs with the above efficiency using combination with a known flexible endoscope.

Modified Example 1

Figure 9:
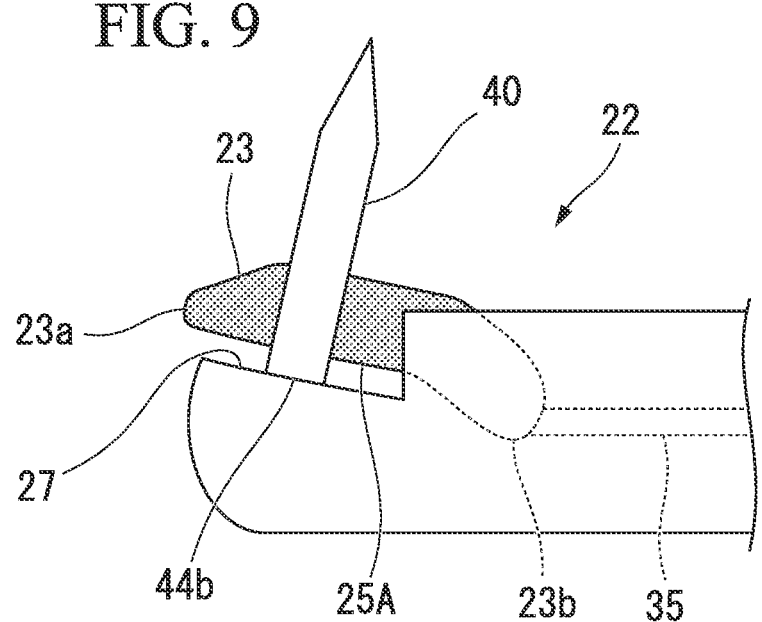
FIG. 9 is a lateral view showing the treatment portion in the needle holder of a modified example of the embodiment.

A modified example of the above first embodiment will be described. FIG. 9 is a lateral view showing the treatment portion in the needle holder of a modified example of the embodiment.

As shown in FIG. 9, the first grasping member 23 of the present modified example includes the first grasping surface 25A. A configuration of the first grasping surface 25A is different from a configuration of the first grasping surface 25 that is disclosed in the above first embodiment.

The first grasping surface 25A of the modified example is bend so as to approach gradually the second grasping member 26 side from the proximal end 23b of the first grasping member 23 to the distal end 23a side in a vicinity of the distal end 23a. The first grasping surface 25A of the modified example limits the movement of the curved needle 40 to the distal end side of the therapeutic portion 22 by the holding force in the state where the curved needle 40 is grasped by the first grasping member 23 and the second grasping member 26. Accordingly, in the present modified example, even if the towing force of the operating wire 35 is large, the curved needle 40 can be reliably grasped by the first grasping member 23 and the second grasping member 26.

Modified Example 2

Figure 10:
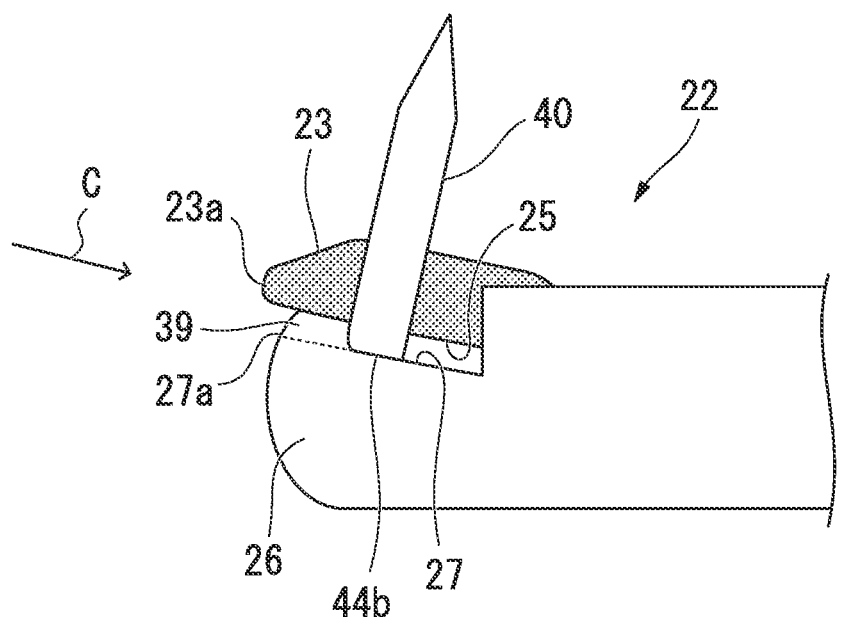
FIG. 10 is a lateral view showing the treatment portion in the needle holder of another modified example of the embodiment.
Figure 11:
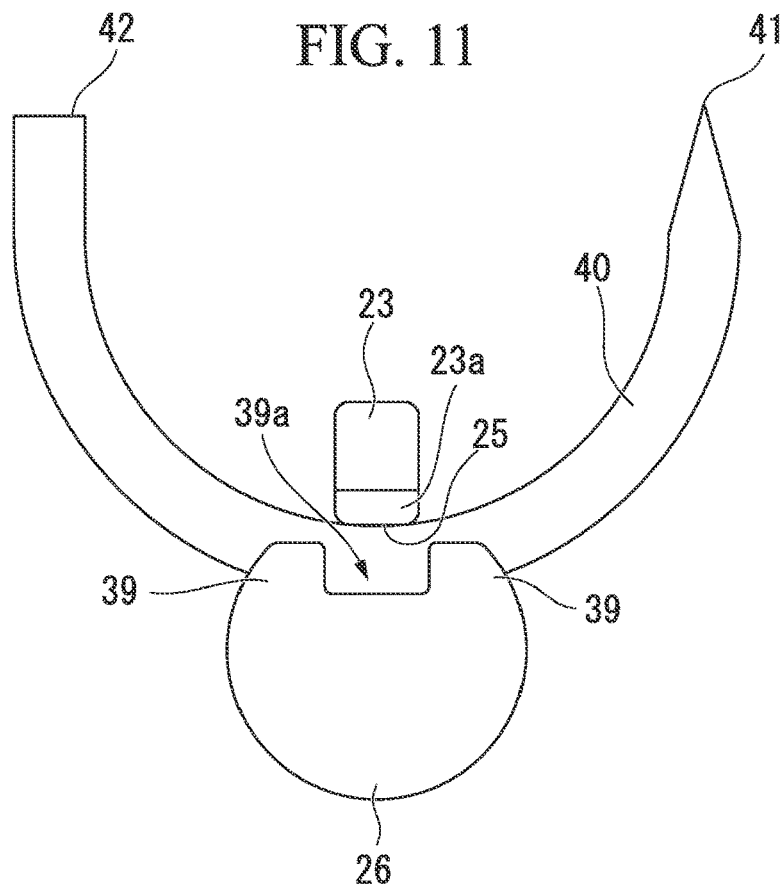
FIG. 11 is a view showing the treatment portion in the needle holder of the modified example of the embodiment from a C direction of FIG. 10.

Another modified example of the above first embodiment will be described. FIG. 10 is a lateral view showing the treatment portion in the needle holder of another modified example of the embodiment. FIG. 11 is a view showing the treatment portion in the needle holder of the modified example of the embodiment from a C direction of FIG. 10.

As shown in FIG. 10 and FIG. 11, the second grasping member 26 of the present modified example includes a projection portion 39 that is projected from the distal end 27a of the second grasping surface 27 to the first grasping surface 25 side.

The projection portion 39 can support the curved needle 40, in the state where the curved needle 40 is grasped by the first grasping member 23 and the second grasping member 26, such that the curved needle 40 moves to the distal end side of the therapeutic portion 22 and the curved needle 40 does not fall from between the first grasping member 23 and the second grasping member 26.

The projection portion 39 of the modified example includes a recessed portion 39a in which the distal end 23a of the first grasping member 23 enters. The recessed portion 39a is provides in the projection portion 39, thereby the curved needle 40 of which a diameter is small than a distance between the second grasping surface 27 to a projection end of the projection portion 39 can be grasped by the first grasping member 23 and the second grasping member 26.

Modified Example 3

Figure 12:
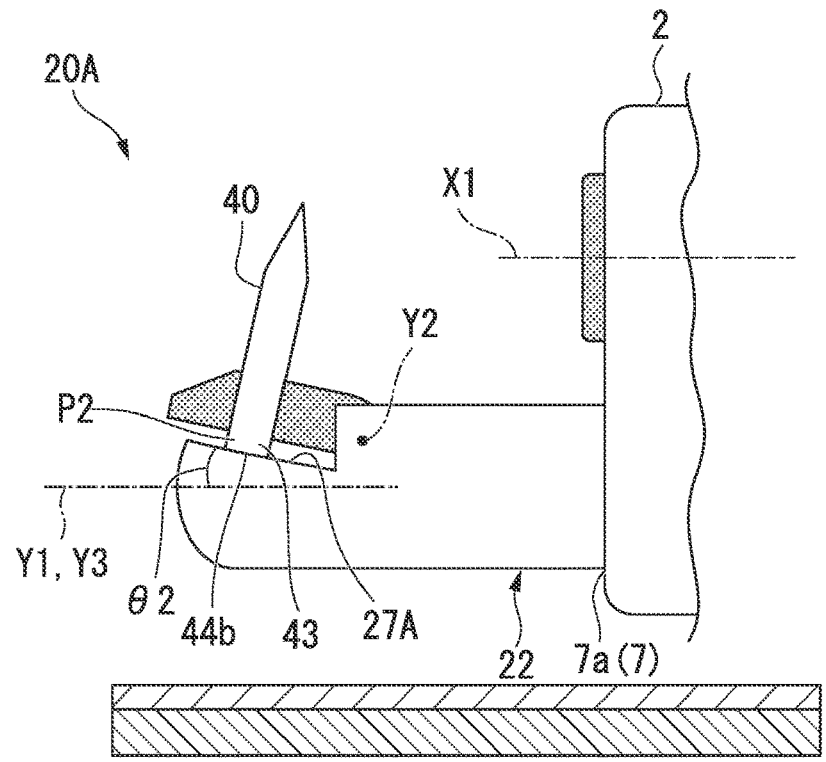
FIG. 12 is a lateral view showing a state where the needle holder of a further another modified example.
Figure 13:
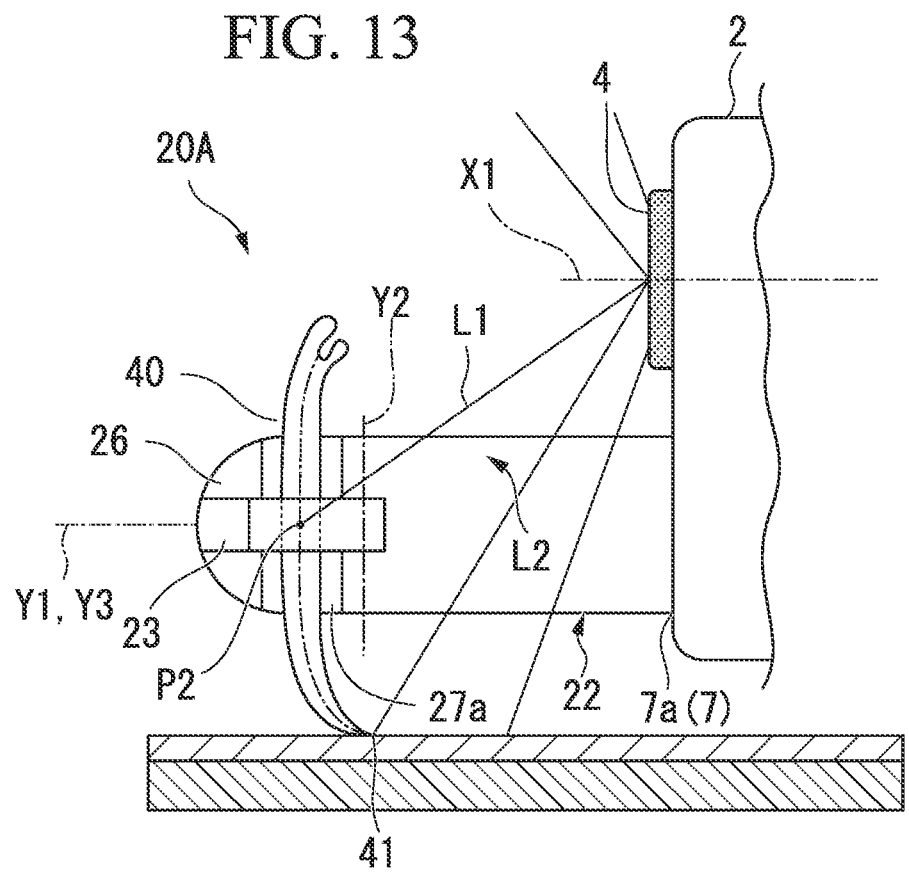
FIG. 13 is a view showing a movement in which the curved needle is grasped and a tissue is sutured using the needle holder of the modified example.

Furthermore another modified example of the above first embodiment will be described. FIG. 12 is a lateral view showing a state where the needle holder of further another modified example. FIG. 13 is a view showing a movement in which the curved needle is grasped and a tissue is sutured using the needle holder of the modified example.

As shown in FIG. 12 and FIG. 13, the suture system 1 of the present modified example includes an optimized needle holder 20A that corresponds to the instrument channel 7 of the flexible endoscope 2 and a configuration of the imager 4.

In the present modified example, a second grasping surface 27A formed in the second grasping member 26, in a state where an arbitrary grasped portion P2 is grasped among the center region P1 of the needle main body 43 of the curved needle 40 between the first grasping member 23 and the second grasping member 26, restricts the orientation of the curved needle 40 such that a first straight-line distance L1 from the imager 4 to the grasped portion P2 is equivalent to a second straight-line distance L2 from the imager 4 to the needle tip 41 of the curved needle 40. The center region P1, for example, is a region from a middle point M between the needle tip 41 and the needle root part 42 on the center line Z1 of the curved needle 40 to a predetermined angle γ to the needle root part 42 side around a center of curvature O1 of the curved needle 40. For example, the predetermined angle γ is 30 degrees.

In the present modified example, the second grasping surface 27A is a constant angle θ2 with respect to the line Y3 that is an extended line of the center line Y1 of the flexible tube 21 when viewing a direction in which the rotation axis Y2 of the therapeutic portion 22 extends. The above constant angle θ2 is set in accordance with a configuration of instrument channel 7 of the flexible endoscope 2 and the imager 4.

In the present modified example, because the second grasping surface 27A is the optimized constant angle θ2 in the configuration of the flexible endoscope 2 that is used along with the needle holder 20 of the e present modified example, in a process of rotating the therapeutic portion 22 around the center line Y1 of the flexible sheath portion 21 and inserting the needle tip 41 into the tissue, a variation of the distance of the needle tip 41 is further reduced on the image captured by the imager 4. Accordingly, in the present modified example, a misconception of a sense of distance of the needle tip 41 in the process of inserting the needle tip 41 into the tissue is hardly to occur.

Second Embodiment

Figure 14:
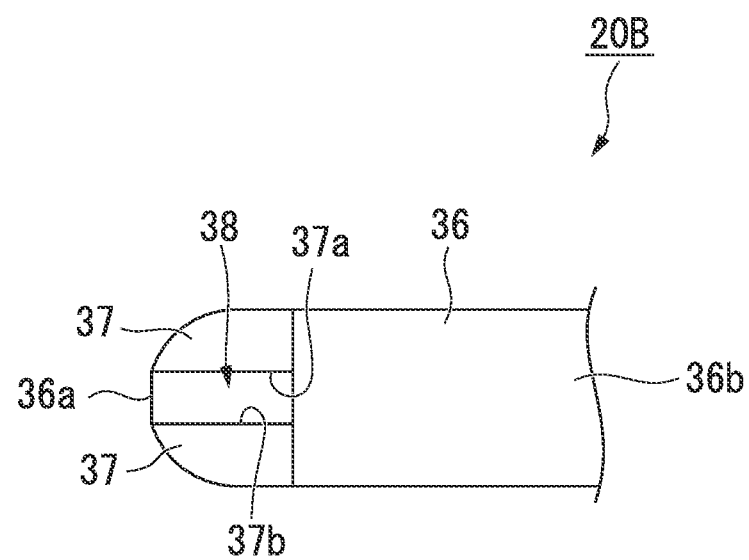
FIG. 14 is a plan view showing a second grasping surface of a needle holder of a second embodiment of the present invention.
Figure 15:
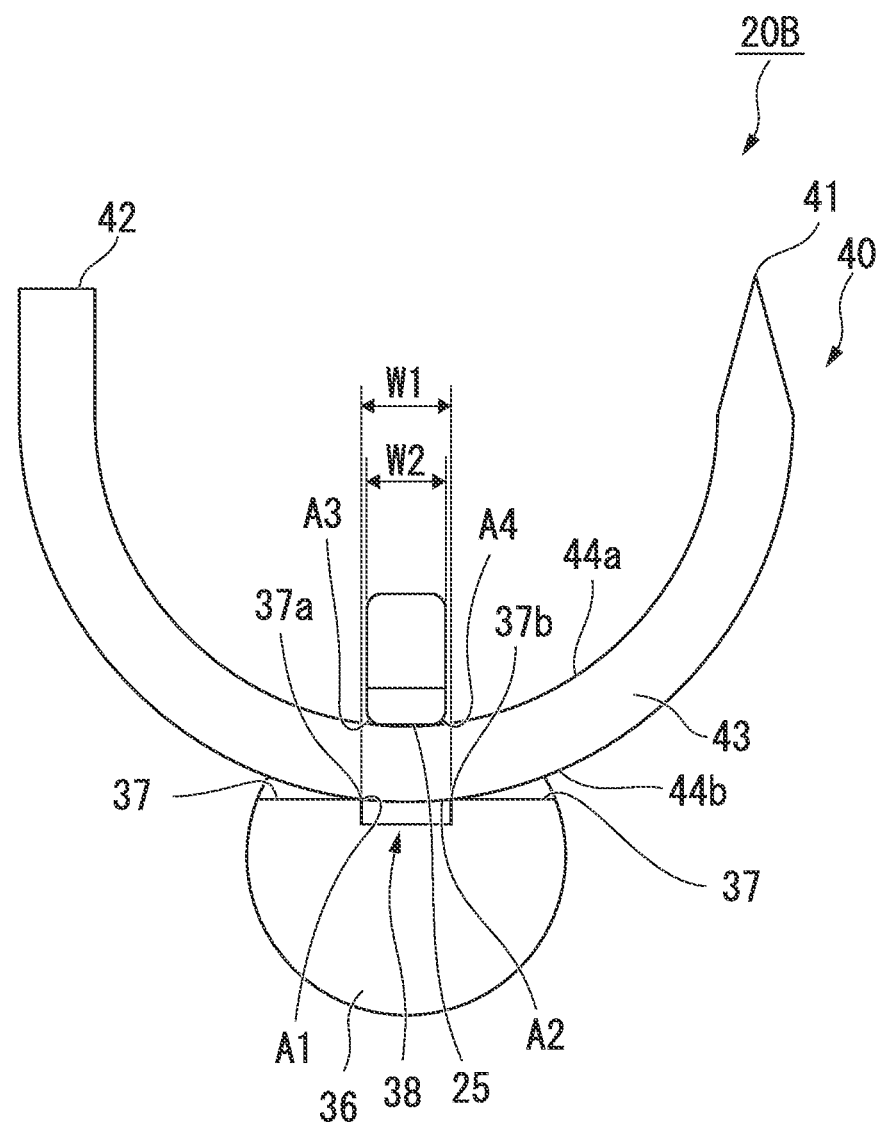
FIG. 15 is a front view showing a treatment portion of the embodiment.

The second embodiment of the present invention will be described. FIG. 14 is a plan view showing a second grasping surface of a needle holder of a second embodiment of the present invention. FIG. 15 is a front view showing a treatment portion of the embodiment.

As shown in FIG. 14 and FIG. 15, the needle holder 20B of the present embodiment a second grasping member 36 instead of the second grasping member 26 disclosed in the above first embodiment. A configuration of the second grasping member 36 is different from that of the second grasping member 26.

The second grasping member 36 of the embodiment includes a second grasping surface 37 that is contacted to the second flat portion 44b of the curved needle 40 similar to the first embodiment. The second grasping member 36 includes a groove part 38 that extends from a distal end 36a of the second grasping member 36 toward a proximal end 36b of the second grasping member 36. In the present embodiment, the second grasping surface 37 is separated into two parts by the groove part 38. The second grasping surface 37 includes the groove part 38 and boundary parts 37a and 37b. In the present embodiment, the boundary parts 37a and 37b is an edge of a groove that extends in a longitudinal direction of the groove part 38 at a position intersecting with the second grasping surface 37 and the groove part 38, the edge may be a corner portion, may be a shape in which the corner portion is chamfered, and may be formed into a round shape instead of the corner portion.

The groove part 38 linearly extends from the distal end 36a of the second grasping member 36 toward the proximal end 36b of the second grasping member 36.

The second flat portion 44b of the curved needle 40 is supported by the boundary parts 37a and 37b by two points (positions indicated by reference signs A1 and A2 in FIG. 15) that is away from each other by contacting the needle main body 43 of the curved needle 40 with the groove part 38 and the boundary parts 37a and 37b of the second grasping 27.

When the first grasping member 23 is closed similar to the above first embodiment in a state where the second flat portion 44b is supported by the boundary parts 37a and 37b, the first grasping member 23 contact to the first flat portion 44a of the curved needle 40. When viewing from the distal end 36a of the second grasping member 36 toward the proximal end 36b of the second grasping member 36, the first flat portion 44a of the curved needle 40 is supported by the first grasping surface 25 of the first grasping member 23 in two portions (positions indicated by reference signs A3 and A4 in FIG. 15) that are positioned to sandwich between the above two portions (A1, A2).

In the present embodiment, because the second flat portion 44b that is formed outside in the curving portion of the curved needle 40 among the outer circumference of the curved needle 40 is supported by the boundary parts 37a and 37b at two portion (A1, A2) that are away from each other, the orientation of the curved needle 40 in the state where the curved needle 40 is grasped by the first grasping member 23 and the second grasping member 36 can be more stable than in the first embodiment.

The embodiment of the present invention will be described based on the drawings. The specific configuration is not limited by this embodiment, other modifications of components can be made without departing from the concept of the invention.

For example, the needle holder 20 disclosed in each embodiment may be used along with an endoscope that is different from the above flexible endoscope 2. For example, the needle holder 20 disclosed in each embodiment may be used along with a side view type endoscope.

Figure 17:
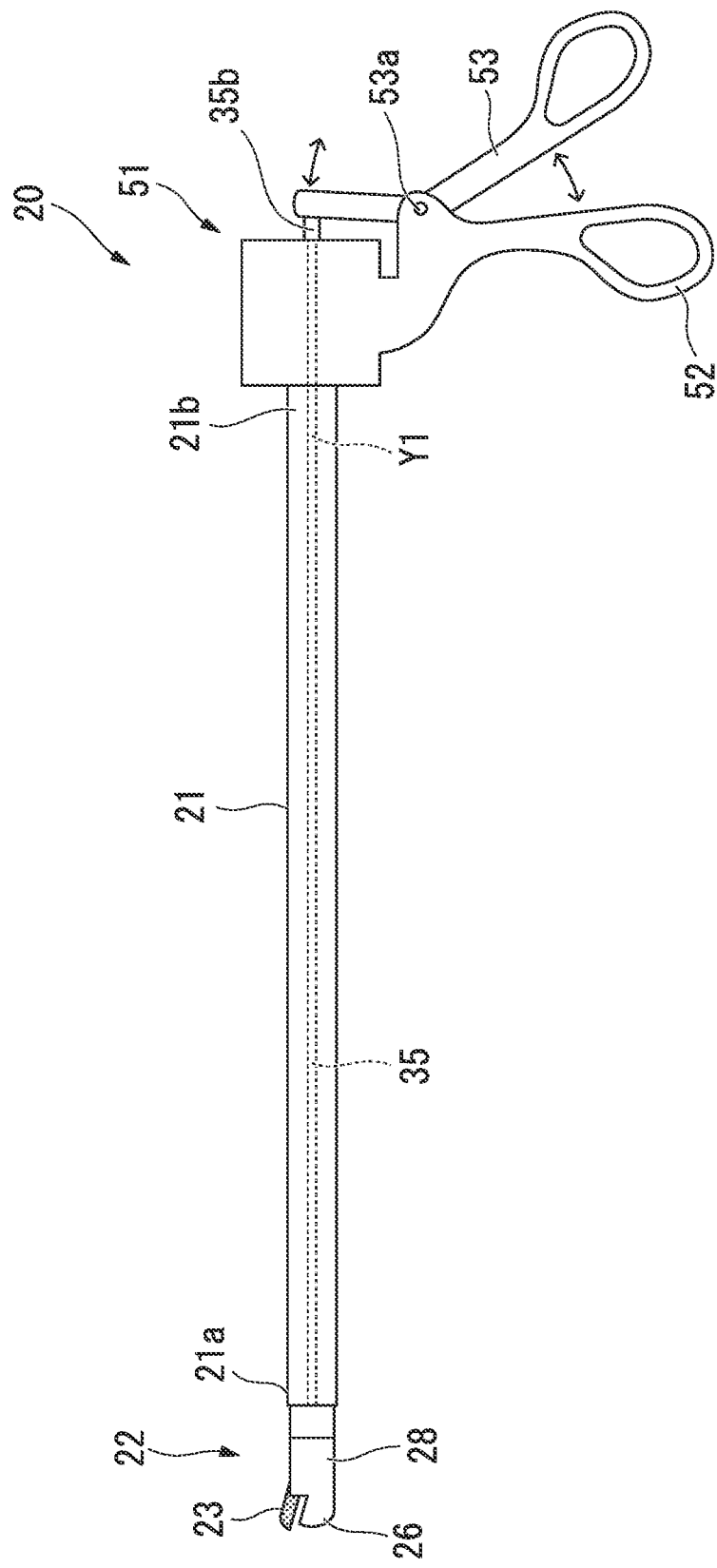
FIG. 17 is a lateral view showing a modified example of a manipulation portion of the needle holder for an endoscope.

The operating portion of the needle holder 20 disclosed in above each embodiment may be a rigid shaft type of forceps like a laparoscopic forceps type in FIG. 17.

For example, as shown in FIG. 17, an operating portion 51 includes a pair of handles (fixing handle 52 and movable handle 53) that are capable of opening and closing, and a fixing mechanism (not shown) that fixes the movable handle 53. The movable handle 53 is coupled with the fixing handle 52 so as to be capable of rotating around a predetermined opening-closing shaft 53a with respect to the fixing handle 52. The movable handle 53 is coupled with the proximal end 35b of the operating wire 35. The operating wire 35 can be moved along the center line Y1 of the flexible sheath portion 21 by opening and closing the movable handle 53 with respect to the fixing handle 52.

Figure 18:
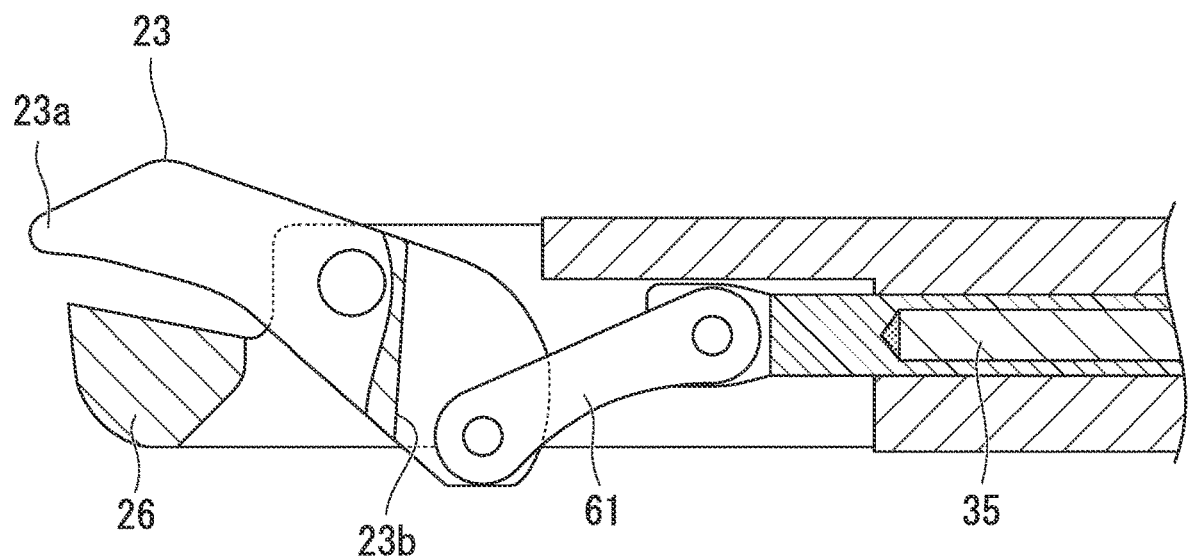
FIG. 18 is a cross-sectional view showing a modified example of a treatment portion of the needle holder for an endoscope.

The proximal end 23b of the first grasping member 23 of the needle holder 20 disclosed in above each embodiment, as shown in FIG. 18, may be coupled with the distal end 35a of the operating wire 35 via a link for coupling 61.

In the above second embodiment, the first grasping member may contact at one point (first flat surface) that is formed in the curved needle.

The effect disclosed in above each embodiment can be obtained even if the needle holder 20 of the above each embodiment combines with a known curved needle and endoscope.

A configuration disclosed in above each embodiment and the modified example may be appropriately combined with each other.

Figure 16:
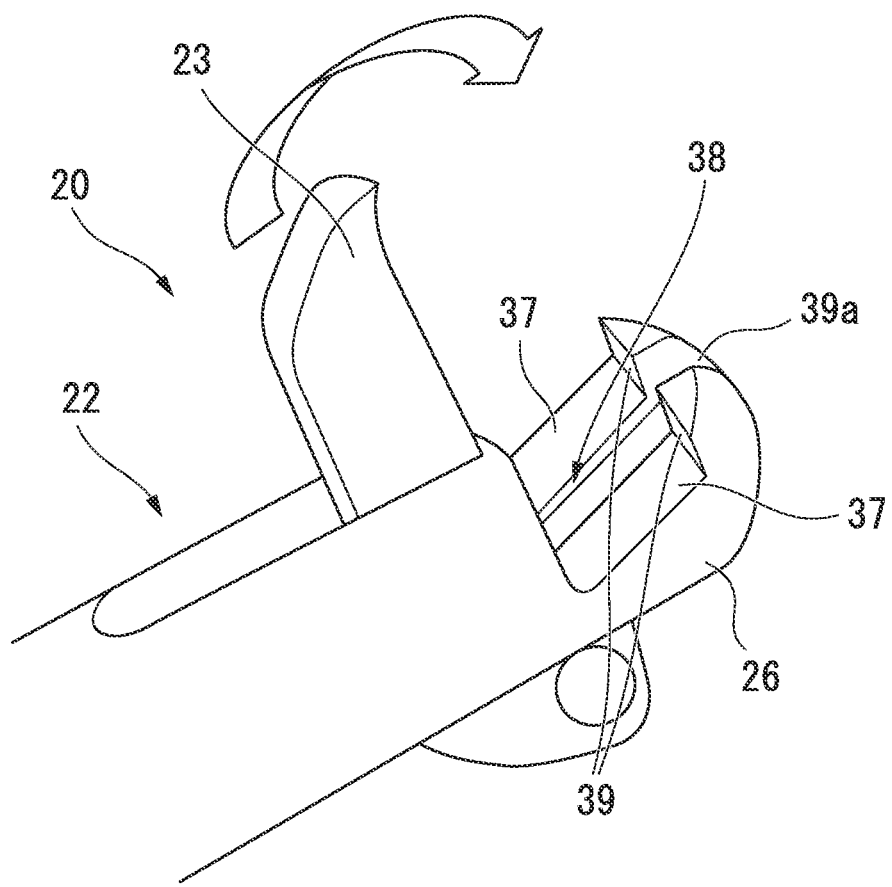
FIG. 16 is a perspective view showing one configuration example of the needle holder of the present invention.

For example, as shown in FIG. 16, the second grasping member 26 disclosed in the above first embodiment may include the groove part 38 and the projection portion 39.

What is claimed is:

1. A needle holder comprising;
   a flexible sheath portion that is longitudinal and flexible, the flexible sheath portion being configured to be inserted into an instrument channel of a flexible endoscope;
   a first grasping member that includes a first grasping surface and is rotatably coupled to a distal end portion of the flexible sheath portion;
   a second grasping member that has a second grasping surface and is provided in the distal end portion of the flexible sheath portion;
   a projection portion that projects from a distal end of the second grasping surface, the projection portion extending toward a surface of the first grasping member;
   a groove that extends from a distal end of the second grasping surface toward a proximal end of the second grasping surface; and
   a bottom surface of the groove extends parallel to a longitudinal axis of the second grasping member and having a same depth from the proximal end of the second grasping surface to the distal end of the second grasping surface.

2. The needle holder according to claim 1, further comprising a curved needle, wherein:
   the first grasping surface and the second grasping surface are flat surfaces and the first grasping surface and the second grasping surface sandwich the curved needle, and
   the projection portion projects from a distal end of the flat surface of the second grasping member toward the first grasping member.

3. The needle holder according to claim 2, wherein the flat surface of the second grasping member includes a first flat surface provided on one side of the groove and a second flat surface provided on an opposite side of the groove.

4. The needle holder according to claim 2, wherein:
   the second grasping surface inclines from a proximal end of the second grasping surface toward a distal end side of the second grasping surface;
   the distal end of the second grasping surface is closer to the first grasping member than the proximal end of the second grasping surface; and
   when a grasped region of a curved needle is grasped by the first grasping surface and the second grasping surface, a needle tip of the curved needle is positioned closer to a proximal end of the flexible sheath portion than the grasped region of the curved needle.

5. The needle holder according to claim 1, wherein:
   the first grasping surface and the second grasping surface are flat surfaces, the first grasping surface and the second grasping surface configured to sandwich a curved needle;
   the second grasping surface inclines from a proximal end of the second grasping surface toward a distal end side of the second grasping surface;
   the distal end of the second grasping surface is closer to the first grasping member than the proximal end of the second grasping surface; and
   when a grasped region of a curved needle is grasped by the first grasping surface and the second grasping surface, a needle tip of the curved needle is positioned closer to a proximal end of the flexible sheath portion than the grasped region of the curved needle.

6. A needle holder comprising:
   a flexible sheath portion that is longitudinal and flexible, the flexible sheath portion being configured to be inserted into an instrument channel of a flexible endoscope;
   a first grasping member that includes a first grasping surface and is rotatably coupled to a distal end portion of the flexible sheath portion; and
   a second grasping member that has a second grasping surface and is provided in the distal end portion of the flexible sheath portion,
   a projection portion that projects from a distal end of the second grasping surface, the projection portion extending toward a surface of the first grasping member, a slit that extends from a distal end of the second grasping surface toward a proximal end of the second grasping surface and a depth of the slit is constant from the proximal end of the second grasping surface to a distal end of the projection portion.

7. The needle holder according to claim 6, further comprising a curved needle, wherein:
the first grasping surface and the second grasping surface are flat surfaces and the first grasping surface and the second grasping surface sandwich the curved needle, and
the projection portion projects from a distal end of the flat surface of the second grasping member toward the first grasping member.

8. The needle holder according to claim 6, wherein: the first grasping surface and the second grasping surface are flat surfaces, the first grasping surface and the second grasping surface configured to sandwich a curved needle;
the second grasping surface inclines from a proximal end of the second grasping surface toward a distal end side of the second grasping surface;
the distal end of the second grasping surface is closer to the first grasping member than the proximal end of the second grasping surface; and
when a grasped region of the curved needle is grasped by the first grasping surface and the second grasping surface, a needle tip of the curved needle is positioned closer to a proximal end of the flexible sheath portion than the grasped region of the curved needle.

9. The needle holder according to claim 6, wherein:
the slit includes a groove that extends from a distal end of the second grasping surface toward a proximal end of the second grasping surface.

10. The needle holder according to claim 9, wherein a flat surface of the second grasping member includes a first flat surface provided on one side of the groove and a second flat surface provided on an opposite side of the groove.

11. The needle holder according to claim 6, wherein:
the second grasping surface inclines from a proximal end of the second grasping surface toward a distal end side of the second grasping surface;
the projection portion is closer to the first grasping member than the proximal end of the second grasping surface; and
when a grasped region of a curved needle is grasped by the first grasping surface and the second grasping surface, a needle tip of the curved needle is positioned closer to a proximal end of the flexible sheath portion than the grasped region of the curved needle.

12. The needle holder according to claim 6, wherein a bottom surface of the slit extends parallel to a longitudinal axis of the second grasping member.

13. A needle holder comprising:
a flexible sheath portion that is longitudinal and flexible, the flexible sheath portion being configured to be inserted into an instrument channel of a flexible endoscope;
a first grasping member that includes a first grasping surface and is rotatably coupled to a distal end portion of the flexible sheath portion; and
a second grasping member that has a second grasping surface and is provided in the distal end portion of the flexible sheath portion,
a projection portion that has a proximal surface and the projection portion that projects from a distal end of the second grasping surface, the projection portion extending toward a surface of the first grasping member,
a slit that extends from a proximal end of the second grasping surface toward a distal end of the second grasping surface and a depth of the slit is constant from the proximal end of the second grasping surface to the proximal surface of the projection portion.

14. The needle holder according to claim 13, further comprising a curved needle, wherein:
the first grasping surface and the second grasping surface are flat surfaces and the first grasping surface and the second grasping surface sandwich the curved needle, and
the projection portion projects from a distal end of the flat surface of the second grasping member toward the first grasping member.

15. The needle holder according to claim 13, wherein:
the first grasping surface and the second grasping surface are flat surfaces, the first grasping surface and the second grasping surface configured to sandwich a curved needle;
the second grasping surface inclines from a proximal end of the second grasping surface toward a distal end side of the second grasping surface;
the distal end of the second grasping surface is closer to the first grasping member than the proximal end of the second grasping surface; and
when a grasped region of the curved needle is grasped by the first grasping surface and the second grasping surface, a needle tip of the curved needle is positioned closer to a proximal end of the flexible sheath portion than the grasped region of the curved needle.

16. The needle holder according to claim 13, wherein:
the slit includes a groove that extends from a distal end of the second grasping surface toward a proximal end of the second grasping surface.

17. The needle holder according to claim 16, wherein a flat surface of the second grasping member includes a first flat surface provided on one side of the groove and a second flat surface provided on an opposite side of the groove.

18. The needle holder according to claim 13, wherein:
the second grasping surface inclines from a proximal end of the second grasping surface toward a distal end side of the second grasping surface;
the projection portion is closer to the first grasping member than the proximal end of the second grasping surface; and
when a grasped region of a curved needle is grasped by the first grasping surface and the second grasping surface, a needle tip of the curved needle is positioned closer to a proximal end of the flexible sheath portion than the grasped region of the curved needle.

19. The needle holder according to claim 13, wherein a bottom surface of the slit extends parallel to a longitudinal axis of the second grasping member.

* * * * *